(12) United States Patent
Kudo

(10) Patent No.: US 10,059,812 B2
(45) Date of Patent: Aug. 28, 2018

(54) METHOD FOR PRODUCING GEL

(71) Applicant: NISSAN CHEMICAL INDUSTRIES, LTD., Tokyo (JP)

(72) Inventor: Yoshihiro Kudo, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/120,555

(22) PCT Filed: Feb. 24, 2015

(86) PCT No.: PCT/JP2015/055221
§ 371 (c)(1),
(2) Date: Aug. 22, 2016

(87) PCT Pub. No.: WO2015/125968
PCT Pub. Date: Aug. 27, 2015

(65) Prior Publication Data
US 2017/0009024 A1 Jan. 12, 2017

(30) Foreign Application Priority Data
Feb. 24, 2014 (JP) ................................. 2014-033098

(51) Int. Cl.
*C08F 20/06* (2006.01)
*C08J 3/075* (2006.01)
(Continued)

(52) U.S. Cl.
CPC .............. *C08J 3/075* (2013.01); *A61K 8/042* (2013.01); *A61K 8/25* (2013.01); *A61K 8/345* (2013.01);
(Continued)

(58) Field of Classification Search
None
See application file for complete search history.

(56) References Cited

FOREIGN PATENT DOCUMENTS

| EP | 3 070 128 A1 | 9/2016 |
| JP | S57-128734 A | 8/1982 |

(Continued)

OTHER PUBLICATIONS

Takeno et al., "Structural and Mechanical Properties of Composite Hydrogel Composed of Polymer and Nanoparticle", Polymer Preprints, Japan, vol. 61, No. 1, p. 683, 2012.
(Continued)

*Primary Examiner* — Richard A Huhn
(74) *Attorney, Agent, or Firm* — Oliff PLC

(57) ABSTRACT

Method for producing a gel having a desired strength, by performing a step of removing a part or all of a solvent. Method for producing a gel containing a water-soluble organic polymer (A), a silicate salt (B), and a dispersant (C) for the silicate salt, including a desolvation step of removing a part or all of one or more solvents selected from the group consisting of water and a water-soluble organic solvent in the gel, or gelling a gel-forming composition containing the water-soluble organic polymer (A), the silicate salt (B), the dispersant (C) for the silicate salt, and one or more solvents selected from the group consisting of water and a water-soluble organic solvent and removing a part or all of the solvent in the composition.

15 Claims, 1 Drawing Sheet

(51) Int. Cl.
| | |
|---|---|
| A61K 8/25 | (2006.01) |
| A61L 27/44 | (2006.01) |
| A61L 27/46 | (2006.01) |
| A61L 15/18 | (2006.01) |
| A61L 15/24 | (2006.01) |
| B01J 13/00 | (2006.01) |
| A61K 8/34 | (2006.01) |
| A61Q 19/00 | (2006.01) |
| A61K 8/81 | (2006.01) |
| A61K 8/04 | (2006.01) |
| C08K 3/34 | (2006.01) |

(52) U.S. Cl.
CPC ............ *A61K 8/8147* (2013.01); *A61L 15/18* (2013.01); *A61L 15/24* (2013.01); *A61L 27/446* (2013.01); *A61L 27/46* (2013.01); *A61Q 19/00* (2013.01); *B01J 13/0069* (2013.01); *C08K 3/34* (2013.01); *C08F 20/06* (2013.01); *C08F 2500/01* (2013.01); *C08J 2333/02* (2013.01)

(56) References Cited

FOREIGN PATENT DOCUMENTS

| JP | S57-195178 A | 11/1982 | |
|---|---|---|---|
| JP | 2002-053762 A | 2/2002 | |
| JP | 2002053762 A | * 2/2002 | |
| JP | 2006-028446 A | 2/2006 | |
| JP | 2006028446 A | * 2/2006 | |
| JP | 2009-127035 A | 6/2009 | |
| JP | 2009-274924 A | 11/2009 | |
| JP | 2011-012107 A | 1/2011 | |
| JP | 2012-016887 A | 1/2012 | |
| TW | 200611714 A | 4/2006 | |
| WO | 91/05736 A1 | 5/1991 | |
| WO | 2014/046127 A1 | 3/2014 | |
| WO | 2014/046136 A1 | 3/2014 | |

OTHER PUBLICATIONS

May 26, 2015 Written Opinion issued in International Patent Application No. PCT/JP2015/055221.

K. Haraguchi et al., "Mechanical Properties of Nanocomposite Hydrogels Consisting of Organic/Inorganic Networks and the Effects of Clay Modification thereto", Network Polymer, vol. 125, No. 1, p. 2-12, 2004.

May 26, 2015 International Search Report issued in International Patent Application No. PCT/JP2015/055221.

Sep. 15, 2017 Extended European Search Report issued in European Patent Application No. 15 752 453.9.

Feb. 7, 2018 Office Action issued in Taiwanese Application No. 104105833.

* cited by examiner

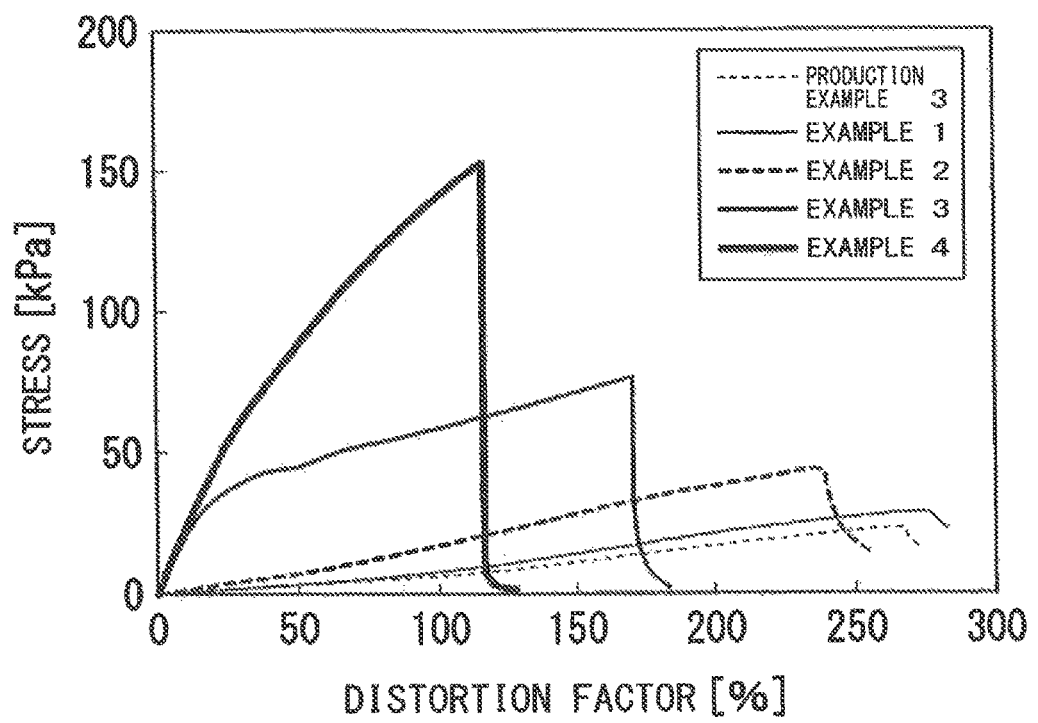

METHOD FOR PRODUCING GEL

TECHNICAL FIELD

The present invention relates to a method for producing a gel, and in particularly, to a method for producing a gel in which the mechanical strength can be adjusted and to which various solvents can be added, by performing a step of removing a part or all of a solvent.

BACKGROUND ART

A gel, particularly a hydrogel contains water as a main component, and therefore, has recently attracted attention from the viewpoint of a soft material having high biocompatibility and a low environmental load. As one example, a self-supporting organic-inorganic composite hydrogel that can be easily produced by mixing a polyelectrolyte, clay particles, and a dispersant at room temperature without a polymerization reaction has been reported (Non-Patent Document 1), In order to enhance the mechanical strength of the hydrogel, the concentration of a solute or a dispersoid has to be increased. However, in the hydrogel described in Non-Patent Document 1, when the concentration of a solute or a dispersoid is increased, the viscosity is extremely increased, and the production of the gel is difficult. For example, a method for forming a gel by uniformly pouring a gel-forming composition in a flow state into a flat container during production of a sheet-shaped gel is desired. However, for the hydrogel produced from a polydectrolyte, clay particles, and a dispersant, when a composition having such flowability that the processing is easy is used, only a sheet-shaped gel having a low strength can be produced.

A dry clay film having a self-standing property (self-supporting property) that contains a polyacrylate salt and a clay mineral is known (Patent Document 1), and a gelled paste is produced as an intermediate. However, this paste does not have a self-supporting property seen in Non-Patent Document 1. Further, this paste is used only as a surface-protection material for purposes of water resistance and heat resistance by applying and drying the paste to form a film, followed by exchange with potassium ions to impart a function of preventing expansion and decomposition of the film that are caused by moisture.

As a method for producing a sheet-shaped hydrogel by drying, the formation of a sheet from polyvinyl alcohol (PVA) as a raw material is known (Patent Document 2). This method is a technique of increasing the strength by layering PVA gel sheets having a low strength. However, an operation of forming a multilayer is complicated.

PRIOR ART DOCUMENTS

Patent Documents

Patent Document 1: Japanese Patent Application Publication No. 2009-274924 (JP 2009-274924 A)
Patent Document 2: Japanese Patent Application Publication No. 201246887 (JP 2012-16887 A)

Non-Patent Document

Non-Patent Document 1: Preprints of the 61st Annual Meeting of the Society of Polymer Science of Japan, Vol. 61, No. 1, p. 683 (2012)

SUMMARY OF THE INVENTION

Problem to be Solved by the Invention

In view of the circumstances, it is an object of the present invention to provide a method for producing a gel to which various organic solvents can be added, which has such flowability that processing is easy at a step of producing a gel, and in which the mechanical strength can be arbitrarily adjusted, and a gel produced by the method.

Means for Solving the Problems

The present inventors have intensively investigated to solve the problems, and as a result, have found that when a solvent is removed from a gel obtained by gelling a gel-forming composition containing a water-soluble organic polymer, a silicate salt, a dispersant for the silicate salt, and the solvent, or the gel-forming composition is gelled and the solvent is removed from the gel-forming composition simultaneously, to increase the solid content concentration, the strength of the obtained gel can be arbitrarily adjusted. Further, the inventors have found that a dried gel obtained by evaporating water and a volatile water-soluble organic solvent in the presence of a non-volatile water-soluble organic solvent retains softness. Moreover, the inventors have found that after the desolvation, when a solvent is added to the gel again to swell the gel, the mechanical strength of the obtained gel is enhanced. Thus, the present invention has been accomplished.

Specifically, as a first aspect, the present invention relates to a method for producing a gel containing a water-soluble organic polymer (A), a silicate salt (B), and a dispersant (C) for the silicate salt, comprising a desolvation step of removing a part or all of one or more solvents selected from the group consisting of water and a water-soluble organic solvent in the gel, or gelling a gel-forming composition containing the water-soluble organic polymer (A), the silicate salt (B), the dispersant (C) for the silicate salt, and one or more solvents selected from the group consisting of water and a water-soluble organic solvent and simultaneously removing a part or all of the solvent in the composition.

As a second aspect, the present invention relates to the method for producing a gel according to the first aspect, wherein the water-soluble organic polymer (A) is a fully or partially neutralized polyacrylate salt having a weight average molecular weight of 1,000,000 to 10,000,000.

As a third aspect, the present invention relates to the method for producing a gel according to the first or second aspect, wherein the silicate salt (B) is water-swellable silicate salt particles selected from the group consisting of smectite, bentonite, vermiculite, and mica.

As a fourth aspect, the present invention relates to the method for producing a gel according to any one of the first to third aspects, wherein the dispersant (C) is one or more selected from the group consisting of sodium orthophosphate, sodium pyrophosphate, sodium tripolyphosphate, sodium tetraphosphate, sodium hexametaphosphate, sodium polyphosphate, sodium poly(meth)acrylate, ammonium poly(meth)acrylate, a sodium acrylate-sodium maleate copolymer, an ammonium acrylate-ammonium maleate copolymer, sodium hydroxide, hydroxylamine, sodium carbonate, sodium silicate, polyethylene glycol, polypropylene glycol, sodium humate, and sodium ligninsulfonate.

As a fifth aspect, the present invention relates to the method for producing a gel according to any one of the first to fourth aspects, wherein the water-soluble organic solvent is methanol, ethanol, propanol, isopropyl alcohol, acetone, glycerin, ethylene glycol, or 1,3-butylene glycol.

As a sixth aspect, the present invention relates to the method for producing a gel according to any one of the first to fourth aspects, wherein the water-soluble organic solvent is a non-volatile water-soluble organic solvent.

As a seventh aspect, the present invention relates to the method for producing a gel according to the sixth aspect, wherein the non-volatile water-soluble organic solvent is glycerin, ethylene glycol, or 1,3-butylene glycol.

As an eighth aspect, the present invention relates to the method for producing a gel according to any one of the first to seventh aspects, wherein the desolvation step is a step of evaporating the solvent.

As a ninth aspect, the present invention relates to the method for producing a gel according to any one of the first to eighth aspects, wherein the desolvation ratio of the solvent in the desolvation step is 25% or more on the basis of the mass of the solvent before desolvation.

As a tenth aspect, the present invention relates to the method for producing a gel according to any one of the first to eighth aspects, wherein the desolvation ratio of the solvent in the desolvation step is set to 90% or more on the basis of the mass of the solvent before desolvation to produce a dried gel.

As an eleventh aspect, the present invention relates to the method for producing a gel according to any one of the first to tenth aspects, comprising a solvent addition step of adding one or more solvents selected from the group consisting of water and a water-soluble organic solvent to the obtained gel after the desolvation step.

As a twelfth aspect, the present invention relates to the method for producing a gel according to the eleventh aspect, wherein the solvent addition step is a step of immersing the gel after the desolvation step in one or more solvents selected from the group consisting of water and a water-soluble organic solvent.

As a thirteenth aspect, the present invention relates to the method for producing a gel according to the eleventh or twelfth aspect, wherein the water-soluble organic solvent is methanol, ethanol, propanol, isopropyl alcohol, acetone, glycerin, ethylene glycol, or 1,3-butylene glycol.

As a fourteenth aspect, the present invention relates to the method for producing a gel according to the eleventh or twelfth aspect, wherein the water-soluble organic solvent is a non-volatile water-soluble organic solvent.

As a fifteenth aspect, the present invention relates to the method for producing a gel according to the fourteenth aspect, wherein the non-volatile water-soluble organic solvent is glycerin, ethylene glycol, or 1,3-butylene glycol.

As a sixteenth aspect, the present invention relates to a gel containing a water-soluble organic polymer (A), a silicate salt (B), and a dispersant (C) for the silicate salt produced by the method according to any one of the first to fifteenth aspects.

As a seventeenth aspect, the present invention relates to a dried gel containing a water-soluble organic polymer (A), a silicate salt (B), and a dispersant (C) for the silicate salt produced by the method according to the tenth aspect.

As an eighteenth aspect, the present invention relates to a method for producing a powder by pulverizing the dried gel according to the seventeenth aspect.

As a nineteenth aspect, the present invention relates to a powder containing a water-soluble organic polymer (A), a silicate salt (B), and a dispersant (C) for the silicate salt produced by the method according to the eighteenth aspect.

Effect of the Invention

As described above, according to the present invention, a gel that has a desirable strength and to which various solvents are added can be produced by preparing a gel-forming composition containing a water-soluble organic polymer, a silicate salt, a dispersant for the silicate salt, and one or more solvents selected from the group consisting of water and a water-soluble organic solvent, gelling the gel-forming composition, and subsequently or simultaneously removing a part or all of the solvent contained in the gel or the gel-forming composition. In order to improve the operativity during production, the amount of the solvent is increased to enhance the flowability of the composition. In this case, the strength of the obtained gel decreases, but the strength is enhanced by the subsequent desolvation. When the amount of desolvation is increased or decreased, the gel strength can be adjusted to a desired gel strength.

In general, a gel in which the most of the solvent is removed loses the flexibility. However, when a non-volatile water-soluble organic solvent is added to a mixture (gel-forming composition) during production, a gel in which the flexibility is maintained even after desolvation is obtained. When the gel is swollen by further adding one or more solvents selected from the group consisting of water and a water-soluble organic solvent to the desolvated gel (highly concentrated or dried gel), the strength of the gel can be enhanced. In a state in which the gel is desolvated (concentrated or dried), the content of the solvent is lower than that in the gel before concentration. Therefore, corrosion or generation of bacteria is suppressed, and storage stability is excellent. During swelling by addition of the solvent, various additives can be added according to an application. For example, a base material for a gel sheet such as a cataplasm has high utility value. Further, the dried gel can be powderized, and can be used as a gel for application of a water retention agent or a refrigerant.

BRIEF DESCRIPTION OF THE DRAWINGS

FIG. 1 is a view showing stress rupture curves in Production Example 3 and Examples 1 to 4.

MODES FOR CARRYING OUT THE INVENTION

The present invention relates to a method for producing a gel having any strength that includes preparing a gel-forming composition containing a water-soluble organic polymer (A), a silicate salt (B), a dispersant (C) for the silicate salt, and one or more solvents selected from the group consisting of water and a water-soluble organic solvent that are components necessary for gelation, and a desolvation step of gelling the gel-forming composition, and subsequently or simultaneously removing the solvent contained in the gel or the gel-forming composition and as gel obtained by the production method. Further, the present invention relates to a method for producing a gel characterized in that one or more solvents selected from the group consisting of water and a water-soluble organic solvent are added after desolvation of a gel-forming composition, to swell the gel, enhancing the strength of the gel, and various solvents are contained, and a gel obtained by the production method.

In the present invention, the gel-forming composition is prepared, for example, by preparing a composition liquid having high flowability (solution and dispersion) in which the components (A), (B), and (C) are dissolved or dispersed at low concentrations to the water, and pouring the solution and the dispersion into a container such as a dish, a pan, and a tray.

The gel of the present invention may contain any other components as necessary, in addition to the aforementioned components, as long as the intended effect of the present invention is not impaired.

<Component (A): Water-Soluble Organic Polymer>

The component (A) of the present invention is a water-soluble organic polymer having an organic acid structure, an organic acid salt structure, or an organic acid anion structure.

Examples of the water-soluble organic polymer (A) having an organic acid structure, an organic acid salt structure, or an organic acid anion structure include, compounds having a carboxyl group such as a salt of poly(meth)acrylic acid, a salt of carboxyvinyl polymer, and a salt of carboxymethyl cellulose; compounds having a sulfonyl group such as a salt of polystyrene sulfonic acid; and compounds having a phosphonyl group such as a salt of polyvinyl phosphonic acid. Examples of the salt include a sodium salt, an ammonium salt, a potassium salt, and a lithium salt. The salt may be a fully or partially neutralized salt. In the present invention, the (meth)acrylic acid refers to both acrylic acid and methacrylic acid.

In the present invention, the water-soluble organic polymer (A) preferably has a carboxylic acid structure, a carboxylate salt structure, or a carboxy anion structure, and may be cross-linked or co-polymerized. Either a fully neutralized salt or a partially neutralized salt can be used.

The weight average molecular weight of the water-soluble organic polymer (A) measured by gel permeation chromatography (GPC) in terms of polyethylene glycol is preferably 1,000,000 to 10,000,000, and more preferably 2,000,000 to 7,000,000.

The weight average molecular weight of water-soluble organic polymer (A) available as a commercial product represented by a weight average molecular weight labelled thereon is preferably 1,000,000 to 10,000,000, and more preferably 2,000,000 to 7,000,000.

In particular, in the present invention, it is preferable that the water-soluble organic polymer (A) is a fully or partially neutralized polyacrylate salt. Specifically, the water-soluble polymer (A) is preferably a fully or partially neutralized sodium polyacrylate, and particularly preferably a fully or partially neutralized non-cross-linked highly polymerized sodium polyacrylate having a weight average molecular weight of 2,000,000 to 7,000,000.

<Component (B): Silicate Salt>

The component (B) of the present invention is a silicate salt, and preferably a water-swellable silicate salt particle.

Examples of the silicate salt (B) include smectite, bentonite, vermiculite, and mica. The silicate salt that forms a colloid with water or a water-containing solvent as a dispersant is preferred. The smectite is a group name of montmorillonite, beidellite, nontronite, saponite, hectorite, stevensite, and the like.

Examples of the Shape of primary particle, of the silicate salt particles include a disc shape, a plate shape, a spherical shape, a particulate shape, a cube, a needle shape, a rod shape, and an amorphous shape. A disc shape or a plate shape having a diameter of 5 nm to 1,000 nm is preferred.

Preferable specific examples of the silicate salt include a layered silicate salt. Examples of the silicate salt easily available as a commercial product include LAPONITE XLG (synthetic hectorite), XLS (synthetic hectorite containing sodium pyrophosphate as a dispersant), XL21 (sodium magnesium fluorosilicate), RD (synthetic hectorite), RDS (synthetic hectorite containing an inorganic polyphosphate salt as a dispersant), and S482 (synthetic hectorite containing a dispersant) available from Rockwood Additives Ltd.; LUCENTITE (registered trademark of Co-op Chemical Co., Ltd.) SWN (synthetic smectite) and SWF (synthetic smectite), micro mica (synthetic mica), and SOMASIF (registered trademark of Co-op Chemical Co., Ltd., synthetic mica) available from Co-op Chemical Co., Ltd.; KUNIPIA (registered trademark of Kunimine Industries Co., Ltd., montmorillonite), and SUMECTON (registered trademark of Kunimine Industries Co., Ltd.) SA (synthetic saponite) available from Kunimine Industries Co., Ltd.; and BENGEL (registered trademark of Hojun Co., Ltd., a refined product of natural bentonite) available from Hojun Co., Ltd.

<Component (C): Dispersant for Silicate Salt>

The component (C) of the present invention is a dispersant for the silicate salt, and preferably a dispersant for water-swellable silicate salt particles.

As the dispersant (C) for the silicate salt, a dispersant or a deflocculant that is used to improve the dispersibility of the silicate salt and delaminate a layered silicate salt can be used.

Examples of the dispersant (C) for the silicate salt include phosphate salt-based dispersants such as sodium orthophosphate, sodium pyrophosphate, sodium tripolyphosphate, sodium tetraphosphate, sodium hexametaphosphate, and sodium polyphosphates; carboxylate salt-based dispersants such as sodium poly(meth)acrylate, ammonium poly(meth)acrylate, a sodium acrylate-sodium maleate copolymer, and an ammonium acrylate-ammonium maleate copolymer; dispersants functioning as an alkali such as sodium hydroxide and hydroxylamine; dispersants forming an insoluble salt or a complex salt by a reaction with polyvalent cations such as sodium carbonate and sodium silicate; and other organic deflocculants such as polyethylene glycol, polypropylene glycol, sodium humate, and sodium ligninsulfonate.

Among them, sodium pyrophosphate as a phosphate salt-based dispersant, low polymerization sodium polyacrylate having a weight average molecular weight of 1,000 to 20,000 as a carboxylate salt-based dispersant, and polyethylene glycol (PEG 900 or the like) as another organic deflocculant are preferred.

It is known that the low polymerization sodium polyacrylate having a weight average molecular weight of 1,000 to 20,000 acts as a dispersant by a mechanism in which the sodium polyacrylate is interacted with silicate salt particles to produce negative charges originated from carboxy anions on the surface of the particles and the silicate salt are dispersed through the repulsion of the charges.

[Preparation of Gel-Forming Composition]

A method for preparing the gel-forming composition used in the present invention is not particularly limited as long as it is a method for mixing components of the water-soluble organic polymer (A), the silicate salt (B), the dispersant (C), and one or more solvents selected from the group consisting of water and a water-soluble organic solvent. Examples thereof include a method for mixing an aqueous solution of the water-soluble organic polymer (A), and an aqueous dispersion of the silicate salt (B) and the dispersant (C) for the silicate salt, and as necessary, further adding one or more water-soluble organic solvents during mixing of the aqueous dispersion or the aqueous solution with the aqueous dispersion.

In the present invention, the aqueous solution and the aqueous dispersion are prepared such that each component is contained at a low content in order to enhance the flowability during processing. Specifically, the concentration of the water-soluble organic polymer (A) in the solution of the water-soluble organic polymer (A) is 0.1% by mass to 1% by mass, the concentration of the silicate salt (B) in the dispersion of the silicate salt (B) and the dispersant (C) for the silicate salt is 0.1% by mass to 3% by mass, and the concentration of the dispersant (C) is 0.01% by mass to 0.5% by mass.

In the method for mixing the components in the aqueous solution or the aqueous dispersion, mechanical or manual stirring or ultrasonication can be used, and the mechanical stirring is preferred. In the mechanical stirring, for example, a magnetic stirrer, a propeller-type stirrer, a planetary centrifugal mixer, a disperser, a homogenizer, a shaker, a vortex mixer, a ball mill, a kneader, a line mixer, an ultrasonic oscillator, or the like can be used. Among them, mixing with a magnetic stirrer, a propeller-type stirrer, a planetary centrifugal mixer, or a line mixer is preferred.

The temperature during mixing of a prepared liquid described above (aqueous solution and aqueous dispersion) is from the freezing point to the boiling point of the aqueous solution or the aqueous dispersion, and is preferably −5° C. to 100° C., and more preferably 0° C. to 50° C.

Examples of the water-soluble organic solvent include, but not particularly limited, water-soluble organic solvents exemplified below.

[Molding Processing of Gel]

The prepared liquid (aqueous solution and aqueous dispersion) can be mixed by pouring each of the aqueous solution and the aqueous dispersion into a container such as a dish, a pan, and a tray. The obtained gel-forming composition can be molding-processed into a gel by holding the prepared liquid in the container followed by gelation. In addition, the gel-forming composition can be processed into a sheet-shaped thin film by applying or spin coating.

In the gelation after the gel-forming composition is held in the container, the upper portion of the container is covered with a lid to prevent evaporation and produce the gel. In addition, the upper portion of the container is opened and the solvent can be evaporated to achieve desolvation (concentration).

The temperature during the gelation is −5° C. to 200° C., and preferably 0° C. to 150° C.

The desolvation of the gel, that is, concentration or drying can be performed by a method in which the gel-forming composition is gelled and simultaneously a solvent content contained in the gel-forming composition is evaporated, or a method of evaporating the solvent content in the gel using the gel that is produced once.

The desolvation can be performed under normal pressure or reduced pressure. The pressure is 0.1 kPa to 100 kPa, and preferably 1 kPa to 100 kPa.

In the present invention, when the desolvation ratio is 20%, and preferably 25% or more, an effect of enhancing the rupture strength of the obtained gel is recognized.

In the present invention, the desolvation ratio is defined as follows.

Desolvation ratio=(mass of gel-forming composition or gel before desolvation−mass of gel after desolvation)/(mass of solvent in gel-forming composition or gel before desolvation)×100

[Taking Out of Dried Gel]

When a non-volatile water-soluble organic solvent is not used especially as the solvent, a highly-concentrated gel (also referred to as dried gel) that has a desolvation ratio of 50% or more is hardened and is likely to stick to the bottom of the container. Therefore, when the gel is taken out from the container as it is, the gel is likely to be impaired and detachment may be difficult. Accordingly, when the obtained gel is immersed in an aqueous solution of an inorganic salt or a mixed solution of a water-soluble organic solvent with water, the gel is easily detached from the container.

The inorganic salt used is a monovalent salt, preferably sodium chloride or lithium chloride, and more preferably sodium chloride.

As the concentration of the inorganic salt is higher, expansion due to permeation of the salt in the dried gel is suppressed. The concentration is preferably 0.1% by mass to 30% by mass, and more preferably 0.5% by mass to 20% by mass.

The water-soluble organic solvent used is alcohol, ketone, amide, nitrile, or the like, preferably an alcohol-based organic solvent, and more preferably methanol, ethanol, propanol, isopropyl alcohol, ethylene glycol, glycerin, or 1,3-butylene glycol, The concentration of the water-soluble organic solvent is preferably 1% by mass to 99% by mass, and more preferably 5% by mass to 80% by mass.

On the other hand, when the non-volatile water-soluble organic solvent is added (to the aqueous solution, the aqueous dispersion, or the mixed liquid of the aqueous solution with the aqueous dispersion) in advance before production of the gel, the flexibility of the gel is maintained even after drying. Therefore, the gel can be taken out from the container without immersing the gel in the solution.

The non-volatile water-soluble organic solvent is preferably a polyhydric alcohol-based organic solvent, and more preferably ethylene glycol, glycerin, or 1,3-butylene glycol.

The concentration of the non-volatile water-soluble organic solvent is preferably 1% by mass to 80% by mass, and more preferably 5% by mass to 50% by mass.

[Addition of Solvent to Gel after Desolvation]

When water is added to the gel after desolvation, the gel is swollen and made flexible. However, when the amount of water to be added is adjusted, the gel that has any concentration and strength can be produced. In a case of a sheet-shaped gel, the gel is stretched in the thickness direction during expansion and further stretched in the plane direction. The sheet-shaped gel is thinner and wider than the original gel. However, as compared with a gel having the same moisture content, the rupture strength of a gel that is subjected to desolvation (drying) and solvent addition is seen to be improved. Further, one or more water-soluble organic solvents or various water-soluble additives can be added to water added during expansion.

[Powderization of Dried Gel]

After a dried gel in which the desolvation ratio is at least 90% or more is produced under a condition where the non-volatile water-soluble organic solvent is not added through a desolvation step of drying the gel, the dried gel is pulverized into a powder. When water is added to the powderized gel, the gel is swollen. Thus, a particulate gel can be obtained. Further, one or more water-soluble organic solvents or various water-soluble additives can be added to water added during swelling.

[Measurement of Strength of Sheet-Shaped Gel]

The strength of the sheet-shaped gel obtained can be measured, for example, by a piercing rupture strength measurement device. For example, the piercing rupture strength can be measured by CREEP METER RE2-33005B manufactured by Yamaden Co., Ltd. A measurement method includes placing a hydrogel sheet between two plates having a circular hole with a diameter of 23 mm, pressing a cylindrical shaft with a diameter of 3 mm (a plunger manufactured by Yamaden Co., Ltd., shape: cylinder, No. 3S, model: P-3S) against the gel from the upper portion of the circular hole at a speed of 1 mm/second, and measuring the stress and the distortion factor until rupture. The rupture stress of the gel obtained in the present invention by the piercing rupture strength measuring device is 5 to 1,000 kPa. For an application requiring strength, the lower limit thereof is 20 kP, 100 kPa, or 300 kPa, and the upper limit thereof is 300 kPa, 500 kPa, or 1,000 kPa. Examples thereof include 20 to 300 kP, and 100 to 1,000 kPa.

EXAMPLES

Hereinafter, the present invention will be described specifically with reference to Examples, but the present invention is not limited to these Examples.

Production Example 1: Production of 9% LAPONITE XLG Aqueous Dispersion 7.5 Parts of low polymerization sodium polyacrylate (JURYMER AC-103, available from TOAGOSEI CO., LTD., weight average molecular weight: 6,000), 3 parts of urea (available from JUNSEI CHEMICAL CO., LTD.), 0.5 parts of phenoxyethanol (available from JUNSEI CHEMICAL CO., LTD.), and 74 parts of water were mixed and stirred at 25° C. until a uniform solution was produced. To the solution, 9 parts of LAPONITE XLG (available from Rockwood Additives Ltd.) was added little by little, the mixture was uniformly dispersed, and 3 parts of 10% aqueous solution of citric acid (available from JUNSEI CHEMICAL CO., LTD.) was then added. The mixture was heated to 80° C. with vigorous stirring, stirred at 80° C. for 30 minutes, and stirred with cooling to 25° C. in an ice-water bath. To the mixture, 3 parts of 10% aqueous solution of citric acid (available from JUNSEI CHEMICAL CO., LTD,) was added, and the mixture was vigorously stirred for 1 hour to obtain a desired product.

Production Example 2: Production of 1.5% Sodium Polyacrylate Aqueous Solution

3 Parts of urea (available from JUNSEI CHEMICAL CO., LTD.), 0.5 parts of phenoxyethanol (available from JUNSEI CHEMICAL CO., LTD.), and 92.5 parts of water were mixed and stirred at 25° C. until a uniform solution was produced. While this solution was vigorously stirred, 1.5 parts of highly polymerized sodium polyacrylate (VISCOMATE NP-800: available from Showa Denko K.K.) was added little by little, and the mixture was vigorously stirred at 25° C. (for 5 hours) until the highly polymerized sodium polyacrylate was completely dissolved, to obtain a desired product.

Production Example 3: Production of Sheet-Shaped Gel 1

To 6 mL of the 9% LAPONITE XLG aqueous dispersion produced in Production Example 1, 6 mL of water was added, and the mixture was stirred at 25° C. for 10 minutes. To this mixture, 12 mL of the 1.5% sodium polyacrylate aqueous solution produced in Production Example 2 was added, and the mixture was vigorously stirred at 25° C. for 1 minute. The mixture was poured uniformly into a dish with a diameter of 9 cm, covered with a lid, and allowed to stand at 25° C. for 48 hours, to obtain a desired product.

Example 1: Production of Sheet-Shaped Gel 2

The sheet-shaped gel 1 produced in Production Example 3 was heated at 40° C. on the dish until the mass was decreased by about 30%, to evaporate moisture (solvent content). Thus, a desired product that was dehydrated (desolvated) by 28.4% was obtained.

Example 2: Production of Sheet-Shaped Gel 3

The sheet-shaped gel 1 produced in Production Example 3 was heated at 40° C. on the dish until the mass was decreased by about 50%, to evaporate moisture. Thus, a desired product that was dehydrated by 49.2% was obtained.

Example 3: Production of Sheet-Shaped Gel 4

The sheet-shaped gel 1 produced in Production Example 3 was heated at 40° C. on the dish until the mass was decreased by about 80%, to evaporate moisture. After cooling, 100 parts of 10% sodium chloride solution was added to the dish, and allowed to stand at 25° C. for 1 hour. The gel was slowly detached from the dish, to obtain a desired product that was dehydrated by 77.5%.

Example 4: Production of Sheet-Shaped Gel 5

The sheet-shaped gel 1 produced in Production Example 3 was heated at 40° C. on the dish until the mass was decreased by 90% or more, to evaporate moisture. After cooling, 100 parts of 10% sodium chloride solution was added to the dish, and allowed to stand at 25° C. for 1 hour. The gel was slowly detached from the dish, to obtain a desired product that was dehydrated by 94%.

Example 5: Production of Sheet-Shaped Gel 6

The sheet-shaped gel 1 produced in Production Example 3 was heated at 40° C. on the dish until the mass was decreased by 90% or more, to evaporate moisture. After cooling, a mixed solution of 50 parts of ethanol with 50 parts of water was added to the dish, and allowed to stand at 25° C. for 1 hour. The gel was slowly detached from the dish, to obtain a desired product that was dehydrated by 93.0%.

Example 6: Production of Sheet-Shaped Gel 7

To 6 mL of the 9% LAPONITE XLG aqueous dispersion produced in Production Example 1, 6 mL, of water and 2.4 mL of glycerin were added, and the mixture was stirred at 25° C. for 10 minutes. To this mixture, 12 mL of the 1.5% sodium polyacrylate aqueous solution produced in Production Example 2 was added, and the mixture was vigorously stirred at 25° C. for 1 minute. The mixture was poured uniformly into a dish with a diameter of 9 cm, and allowed to stand at 25° C. for 48 hours without covering in an open state. A desired product that was dehydrated by 90.6% was obtained. The sheet-shaped gel on the dish was able to be detached from the dish as it was.

Example 7: Production of Sheet-Shaped Gel 8

The sheet-shaped gel 1 produced in Production Example 3 was heated at 40° C. on the dish until the mass was decreased by 90% or more, to evaporate moisture. The gel was dehydrated to 93.2% and cooled, water in an amount of decreased water was added, and the mixture was allowed to stand at 25° C. for 24 hours, to obtain a desired product.

Example 8: Production of Sheet-Shaped Gel 9

The sheet-shaped gel 1 produced in Production Example 3 was heated at 40° C. on the dish until the mass was decreased by 90% or more, to evaporate moisture. The gel was dehydrated to 96.5% and cooled, water in an amount of 50% of the dehydration was added, and the mixture was allowed to stand at 25° C. for 24 hours, to obtain a desired product.

Example 9: Piercing Strength Test on Sheet-Shaped Gel

The sheet-shaped gels produced in Examples 1 to 8 and Production Example 3 were subjected to measurement of piercing strength. In a measurement method, using CREEP METER RE2-33005B manufactured by Yamaden Co., Ltd., a hydrogel sheet was placed between two plates having a circular hole with a diameter of 23 mm, a cylindrical shaft with a diameter of 3 mm (a plunger manufactured by Yamaden Co., Ltd., shape: cylinder, No. 38, model: P-3S) was pressed against the hydrogel sheet from the upper portion of the circular hole at a speed of 1 min/second, and the stress and the distortion factor until rupture were measured. The measurement results are shown in Table 1. A comparison graph of stress-distortion curves of the sheet-shaped gels produced in Examples 1 to 4 and Production Example 3 is shown in FIG. 1. As compared with the gel in Production Example 3 in which desolvation was not performed, the rupture stress in all of the gels in which desolvation was performed was seen to be improved, that was, the gel strength was seen to be improved. In comparison of Examples 1 to 4, as the desolvation ratio was raised, and the gel strength was increased. In the gel of Example 7 (desolvation ratio: 0%) in which a solvent was added again after desolvation, the rupture stress was higher than that in the gel of Production Example 3 in which the desolvation ratio was the same. Thus, an effect of enhancing the strength by a process of adding a solvent after desolvation was confirmed. The same effect was also confirmed in comparison of Example 2 (desolvation ratio: 49.2%; the process of adding a solvent was not performed) and Example 8 (desolvation ratio: 50%; the process of adding a solvent was performed).

TABLE 1

| Example | Desolvation ratio (%) | Rupture stress (kPa) | Rupture distortion factor (%) |
| --- | --- | --- | --- |
| Production Example 3 | 0 | 23.17 | 267 |
| Example 1 | 28.4 | 29.00 | 274 |
| Example 2 | 49.2 | 43.43 | 237 |
| Example 3 | 77.5 | 76.68 | 170 |
| Example 4 | 94.4 | 152.2 | 115 |
| Example 5 | 93.0 | 163.1 | 147 |
| Example 6 | 90.6 | 115.0 | 67 |
| Example 7 | 0 | 33.37 | 245 |
| Example 8 | 50.0 | 67.62 | 117 |

INDUSTRIAL APPLICABILITY

The gel of the present invention can be easily produced, and the viscoelasticity such as rupture strength and deformation ratio of the gel can be adjusted by adjusting the solid content concentration by evaporation of solvent content. The obtained gel has high transparency and stretchability, and is easy in processing. Various water-soluble organic solvents can be added to the gel. The gel can be applied to various products using the properties thereof.

Examples of the products include medical materials including external medicine base materials such as wound dressing, cataplasms, and hemostatic materials, sealant materials for surgery, scaffolding materials for regenerative medicine, implant materials such as artificial corneas, artificial lenses, artificial vitreous bodies, artificial skin, artificial joints, artificial cartilage, and materials for breast augmentation, and materials for soft contact lenses, medium materials for tissue culturing, microbial culturing, and the like, cosmetic materials such as sheets for packing, sanitary materials such as diapers for children and adults and sanitary napkins, gel materials for aromatics and deodorants, confectionery and gum materials for dogs, materials for chromatographic carriers, materials for bioreactor carriers, materials for separation function membranes, building/construction materials such as noncombustible materials for construction, fire-resistant covering materials, humidity control materials, refrigerants, seismic buffer materials, mudflow preventing materials, and sandbags, greening materials such as soil water retention agents, raising media, and agricultural and horticultural hydroponic supports, toy materials such as children's toys and models, materials for stationeries, shock absorbing materials for sporting goods such as sports shoes and protectors, cushion materials for shoe soles, buffer materials for bulletproof vests, buffer materials for automobiles and the like, buffer materials for transportation, packing materials, buffering/protecting mat materials, shock buffering materials within electronic devices, buffer materials for transporting wagons for precision components such as optical devices and semiconductor-related components, vibration-proof/damping materials for industrial equipment, sound reduction materials for industrial equipment such as motor-using equipment and compressors, coating materials for frictional parts of environment-conscious material apparatuses such as rubber alternative materials for tires and rubber bands and alternative materials for plastics, coating additives, waste disposal such as gelators for waste mud and lost circulation preventing agents, adhesive materials, sealants for sealing, electronic materials such as gel electrolyte materials for primary cells, secondary cells, and capacitors, gel electrolyte materials for dye-sensitized solar cells, and materials for fuel cells, and materials for photographic films.

The invention claimed is:

1. A method for producing a gel containing a water-soluble organic polymer (A), a silicate salt (B), and a dispersant (C) for the silicate salt, comprising
a desolvation step of removing a part or all of one or more solvents selected from the group consisting of water and a water-soluble organic solvent in the gel, or
gelling a gel-forming composition containing the water-soluble organic polymer (A), the silicate salt (B), the dispersant (C) for the silicate salt, and one or more solvents selected from the group consisting of water and a water-soluble organic solvent and removing a part or all of the solvent in the composition,
wherein the water-soluble organic polymer (A) is a fully or partially neutralized polyacrylate salt having a weight average molecular weight in a range of from 1,000,000 to 10,000,000.

2. The method for producing a gel according to claim 1, wherein the silicate salt (B) is water-swellable silicate salt particles selected from the group consisting of smectite, bentonite, vermiculite, and mica.

3. The method for producing a gel according to claim 1, wherein the dispersant (C) is one or more selected from the group consisting of sodium orthophosphate, sodium pyrophosphate, sodium tripolyphosphate, sodium tetraphosphate, sodium hexametaphosphate, sodium polyphosphate, sodium poly(meth)acrylate, ammonium poly(meth)acrylate, a sodium acrylate-sodium maleate copolymer, an ammonium acrylate-ammonium maleate copolymer, sodium hydroxide, hydroxylamine, sodium carbonate, sodium silicate, polyethylene glycol, polypropylene glycol, sodium humate, and sodium ligninsulfonate.

4. The method for producing a gel according to claim 1, wherein the water-soluble organic solvent is methanol, ethanol, propanol, isopropyl alcohol, acetone, glycerin, ethylene glycol, or 1,3-butylene glycol.

5. The method for producing a gel according to claim 1, wherein the water-soluble organic solvent is a polyhydric alcohol-based organic solvent.

6. The method for producing a gel according to claim 5, wherein the polyhydric alcohol-based organic solvent is glycerin, ethylene glycol, or 1,3-butylene glycol.

7. The method for producing a gel according to claim 1, wherein the desolvation step is a step of evaporating the solvent.

8. The method for producing a gel according to claim 1, wherein the desolvation ratio of the solvent in the desolvation step is 25% or more on the basis of the mass of the solvent before desolvation.

9. The method for producing a gel according to claim 1, wherein the desolvation ratio of the solvent in the desolvation step is set to 90% or more on the basis of the mass of the solvent before desolvation to produce a dried gel.

10. The method for producing a gel according to claim 1, further comprising a solvent addition step of adding one or more solvents selected from the group consisting of water and a water-soluble organic solvent to the obtained gel after the desolvation step.

11. The method for producing a gel according to claim 10, wherein the solvent addition step is a step of immersing the gel after the desolvation step in one or more solvents selected from the group consisting of water and a water-soluble organic solvent.

12. The method for producing a gel according to claim 10, wherein the water-soluble organic solvent is methanol, ethanol, propanol, isopropyl alcohol, acetone, glycerin, ethylene glycol, or 1,3-butylene glycol.

13. The method for producing a gel according to claim 10, wherein the water-soluble organic solvent is a polyhydric alcohol-based organic solvent.

14. The method for producing a gel according to claim 13, wherein the polyhydric alcohol-based organic solvent is glycerin, ethylene glycol, or 1,3-butylene glycol.

15. A method for producing a powder comprising:

performing the method according to claim 9 to produce a dried gel, and pulverizing the dried gel.

* * * * *